US011761875B2

(12) United States Patent
Gasparella et al.

(10) Patent No.: US 11,761,875 B2
(45) Date of Patent: Sep. 19, 2023

(54) ADJUSTING FOR AIR FLOW TEMPERATURE CHANGES IN AN ASPIRATING SMOKE DETECTOR

(71) Applicant: Honeywell International Inc., Charlotte, NC (US)

(72) Inventors: Simone Gasparella, Trieste (IT); Domenico Piro, Trieste (IT); Erika Simeoni, Staranzano (IT)

(73) Assignee: Honeywell International Inc., Charlotte, NC (US)

( * ) Notice: Subject to any disclaimer, the term of this patent is extended or adjusted under 35 U.S.C. 154(b) by 179 days.

(21) Appl. No.: 17/335,273

(22) Filed: Jun. 1, 2021

(65) Prior Publication Data

US 2022/0381667 A1 Dec. 1, 2022

(51) Int. Cl.
| | |
|---|---|
| *G01N 33/00* | (2006.01) |
| *G01K 13/024* | (2021.01) |
| *G08B 17/10* | (2006.01) |
| *G01N 15/06* | (2006.01) |
| *F04D 27/00* | (2006.01) |
| *G01N 29/00* | (2006.01) |
| *G08B 29/04* | (2006.01) |
| *F24F 11/00* | (2018.01) |

(52) U.S. Cl.
CPC ........... *G01N 15/06* (2013.01); *F04D 27/004* (2013.01); *G01K 13/024* (2021.01); *G01N 29/00* (2013.01); *G01N 33/0016* (2013.01); *G08B 29/043* (2013.01); *F24F 11/00* (2013.01); *G01N 2015/0693* (2013.01); *G08B 17/10* (2013.01)

(58) Field of Classification Search
CPC .. G01K 13/024; G01N 33/0016; G01N 15/06; G08B 29/043; G08B 17/10
See application file for complete search history.

(56) References Cited

U.S. PATENT DOCUMENTS

| | | | |
|---|---|---|---|
| 4,494,055 A * | 1/1985 | Bitting ..................... | H02P 6/30 416/5 |
| 4,772,131 A * | 9/1988 | Varela .................... | G01K 11/24 374/119 |
| 5,738,706 A * | 4/1998 | Swanander .......... | B01D 46/446 55/467 |
| 8,098,166 B2 * | 1/2012 | Lang ..................... | G08B 17/10 340/630 |

(Continued)

FOREIGN PATENT DOCUMENTS

| | | |
|---|---|---|
| CN | 1256411 | 6/2000 |
| CN | 110613912 A | 12/2019 |

(Continued)

*Primary Examiner* — John A Tweel, Jr.
(74) *Attorney, Agent, or Firm* — Brooks, Cameron & Huebsch, PLLC

(57) ABSTRACT

Methods, devices, and systems for adjusting for air flow temperature changes in an aspirating smoke detector are described herein. In some examples, one or more embodiments include a blower configured to cause air to flow through the aspirating smoke detector, and a controller configured to determine a temperature of the air flowing through the aspirating smoke detector has changed by a particular amount and adjust a speed of the blower in response to compensate the air flowing through the aspirating smoke detector that has changed by the particular amount.

20 Claims, 5 Drawing Sheets

(56) References Cited

U.S. PATENT DOCUMENTS

| | | |
|---|---|---|
| 9,134,716 B2 | 9/2015 | Cole et al. |
| 9,269,248 B2 * | 2/2016 | Luterotti .................. B05B 1/00 |
| 9,576,458 B2 * | 2/2017 | Calvert ................. G08B 17/10 |
| 9,824,564 B2 | 11/2017 | Bressanutti et al. |
| 10,115,280 B2 | 10/2018 | Bressanutti et al. |
| 10,161,837 B2 * | 12/2018 | Ajay .................... G08B 17/113 |
| 10,877,011 B2 | 12/2020 | Cummings et al. |
| 11,244,551 B2 * | 2/2022 | Escofet Via ........... G08B 17/10 |
| 2013/0238138 A1 | 9/2013 | Cole et al. |
| 2020/0116688 A1 | 4/2020 | Bertini et al. |
| 2021/0348987 A1 * | 11/2021 | Moix Olive ......... G08B 17/107 |

FOREIGN PATENT DOCUMENTS

| | | |
|---|---|---|
| DE | 29518042 U1 | 1/1996 |
| DE | 19605637 C1 | 5/1997 |
| EP | 0696787 | 6/1999 |

* cited by examiner

ADJUSTING FOR AIR FLOW TEMPERATURE CHANGES IN AN ASPIRATING SMOKE DETECTOR

TECHNICAL FIELD

The present disclosure relates to methods, devices, and systems for adjusting for air flow temperature changes in an aspirating smoke detector.

BACKGROUND

Large facilities (e.g., buildings), such as commercial facilities, office buildings, hospitals, and the like, may have an alarm system that can be triggered during an emergency situation, such as, for instance, a fire, to warn occupants to evacuate the facility. Such alarm systems may rely on detection systems, such as an aspirating smoke detection system, to detect a fire. An aspirating smoke detection system can include a plurality of aspirating smoke detectors, located throughout the facility (e.g., on different floors and/or in different rooms of the facility), that can detect a hazard event, such as smoke generation (e.g., as the result of a fire or otherwise), and provide a notification (e.g., to a control panel and/or alarms of the alarm system) of the detected hazard event.

An aspirating smoke detector can have a detection unit which draws air through a network of pipes to detect smoke. For example, a facility may utilize a series of pipes located throughout the facility that can draw air from various spaces in the facility to the detection unit to detect smoke.

DETAILED DESCRIPTION

Figure 1A:
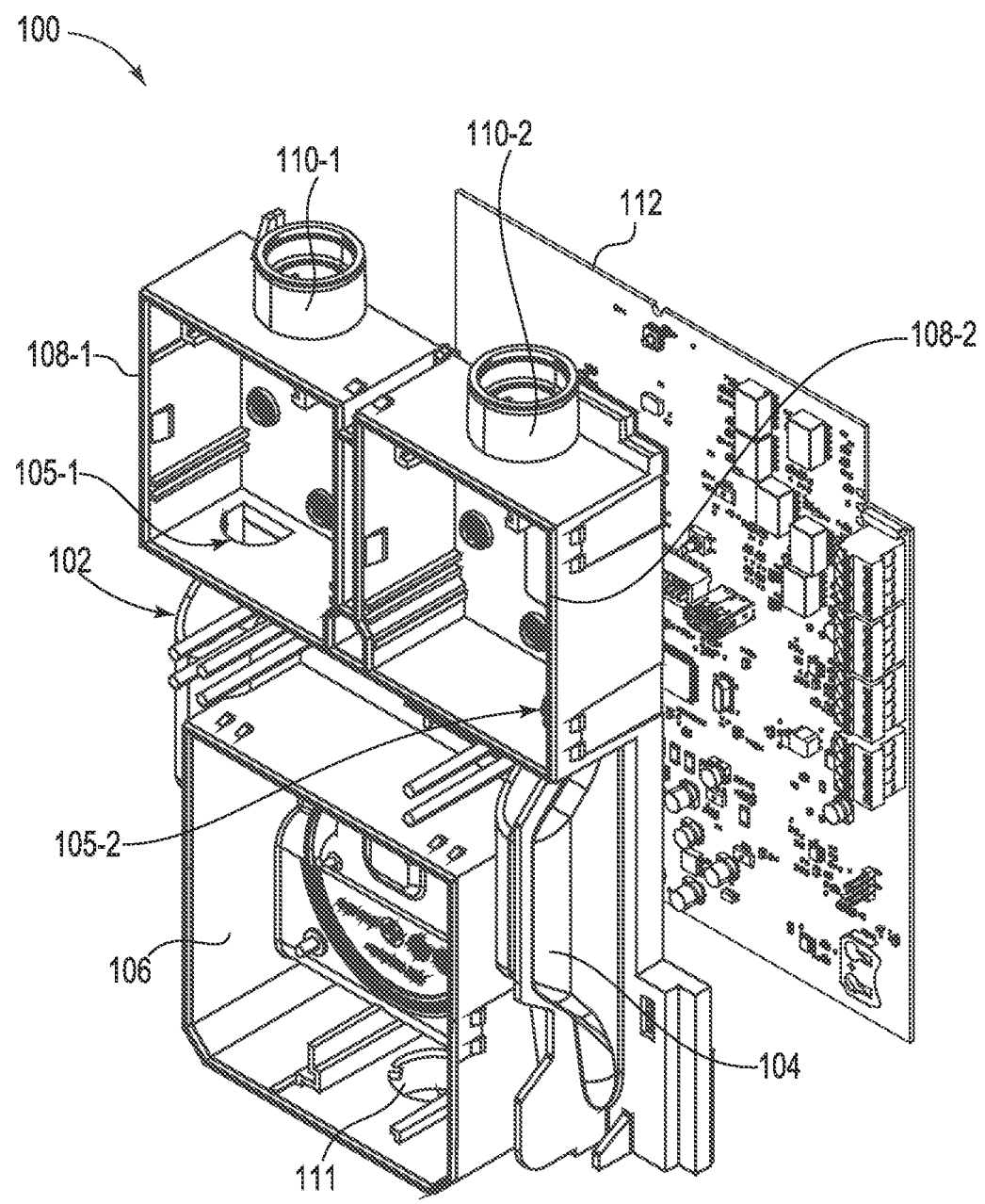
FIG. 1A is an exploded view of an example of a portion of an aspirating smoke detector device, in accordance with one or more embodiments of the present disclosure

Methods, devices, and systems for adjusting for air flow temperature changes in an aspirating smoke detector are described herein. In some examples, one or more embodiments include a blower configured to cause air to flow through the aspirating smoke detector, and a controller configured to adjust the speed of the blower in response to a particular amount of air flow temperature change and determining if it has changed by a particular (e.g., correct) amount.

An aspirating smoke detector device can be utilized in a facility to detect a hazard event by detecting the presence of smoke. The aspirating smoke detector device can draw gas (e.g., air, via a blower) from the facility into a sensor through a network of pipes throughout the facility. The sensor can sample the gas in order to determine whether the gas includes smoke particles. In response to detection of smoke particles, the aspirating smoke detector device can transmit a signal to a control panel in the facility to signal detection of smoke particles.

During the operation of the aspirating smoke detector device, the detector can monitor the air flow through the detector (e.g., through the flow channels of the detector) to ensure there are no air flow faults associated with the detector (e.g., no obstacles are blocking the detector, there are no leaks in the pipes, etc.). For instance, if the air flow through the detector is outside of a particular (e.g., reference) airflow range (e.g., exceeds an upper air flow fault limit or drops below a lower air flow fault limit), this can be an indication of an air flow fault, and the detector can provide an indication (e.g., notification) of an air flow fault upon detecting such an occurrence.

In some instances, however, the temperature of the air flowing through the detector can change (e.g., increase or decrease), and this change in temperature can cause a variation of the air flow through the detector. For example, a significant enough change in the air flow temperature can cause a variation of the air flow itself and the detector to detect that the air flow is outside the reference air flow range, which in turn can cause the detector to provide an indication of an air flow fault. Since it is the blower inside the detector that changes its behavior while the temperature of the air flow changes and there is no air flow fault (e.g., no obstacles are blocking the detector, there are no leaks in the pipes, etc.), such an instance can be referred to herein as a false air flow fault, and can cause unwanted consequences, such as activation of other components (e.g., relays, LEDs, etc.) of the alarm system of the facility, and can be difficult and/or time consuming to identify (e.g., distinguish from a real air flow fault) and remedy.

Aspirating smoke detectors of the present disclosure, however, can prevent such false air flow faults from occurring by adjusting (e.g., compensating) for changes that occur in the temperature of the air flowing through the detector. For example, upon determining that the air flow temperature has changed by a particular amount, an aspirating smoke detector of the present disclosure can adjust the speed of its blower, which can adjust the speed of the air flow through the detector to compensate for the temperature change, which in turn can prevent the temperature change from causing false air flow fault from occurring. Accordingly, aspirating smoke detectors of the present disclosure can avoid the unwanted consequences and difficulties caused by false air flow faults.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 106 may reference element "07" in FIGS. 1A-1C, and a similar element may be referenced as 207 in FIG. 2.

As used herein, "a", "an", or "a number of" something can refer to one or more such things, while "a plurality of" something can refer to more than one such things. For example, "a number of components" can refer to one or more components, while "a plurality of components" can refer to more than one component.

FIG. 1A is an exploded view of an example of a portion of an aspirating smoke detector device 100, in accordance with one or more embodiments of the present disclosure. The aspirating smoke detector device 100 can include a manifold 102 and a PCB 112.

As illustrated in FIG. 1A, the aspirating smoke detector device 100 can include a printed circuit board (PCB) 112. As used herein, the term "PCB" refers to a device to mechanically support and electrically connect electrical components via conductive traces. The PCB 112 can, therefore, include electrical components utilized in detection of smoke via the aspirating smoke detector device 100. For example, although not illustrated in FIG. 1A for clarity and so as not to obscure embodiments of the present disclosure, the aspirating smoke detector device 100 can include a blower and sensor head housings. The PCB 112 can be utilized to control the blower (e.g., the speed of the blower), receive signals from the sensor head housings, etc. The PCB 112 can, accordingly, be utilized to control operation of the aspirating smoke detector device 100 to detect smoke particles in a gas (e.g., air) flowing through the aspirating smoke detector device 100 and transmit a signal to a control panel in response to detection of smoke particles in the gas. The PCB 112 can also be utilized and/or include a controller to adjust for air flow temperature changes in the air flowing through the aspirating smoke detector device 100, as will be further described herein.

As shown in the exploded view of FIG. 1A, the aspirating smoke detector device 100 can further include a manifold 102. For example, the manifold 102 can make up a portion of the aspirating smoke detector device 100 and can include various parts, including a flow path 104, a blower housing 106, a first sensor head housing 108-1, and a second sensor head housing 108-2, as are further described herein. The manifold 102 can be a plastic material. For example, the manifold 102 can be manufactured from acrylonitrile butadiene styrene (ABS) plastic, poly(methyl methacrylate) (PMMA) plastic, thermoplastic elastomers (TPE), among other types of plastic materials. However, embodiments are not so limited, and the housing 102 can be made of any other type of material (e.g., metal, carbon fiber, etc.).

A flow path 104 can be included as part of the manifold 102. As used herein, the term "manifold" refers to a device having a chamber including at least one inlet and at least one outlet. The flow path 104 can include a first flow channel 105-1 and a second flow channel 105-2 (referred to collectively herein as flow channels 105). The flow channels 105 can allow for the flow of gas (e.g., air) through the aspirating smoke detector device 100. For instance, gas can flow into and out of different portions of the aspirating smoke detector device 100 through the flow channels 105 for smoke detection.

The manifold 102 can include a blower housing 106. The blower housing 106 can be configured to receive a blower (e.g., not illustrated in FIG. 1A). The blower can operate to draw gas into and cause gas to flow through the aspirating smoke detector device 100. The blower housing 106 can include a blower housing outlet 111. The gas flowing through the aspirating smoke detector device 100 can exit the aspirating smoke detector device through the blower housing outlet 111.

The first flow channel 105-1 can connect the blower housing 106 to a first sensor head housing 108-1. The first sensor head housing 108-1 can be configured to receive a sensor head (e.g., not illustrated in FIG. 1A). The first sensor head housing 108-1 can include a first sensor head housing inlet 110-1. The blower can operate to draw gas into a sensor head located in the first sensor head housing 108-1 via the first sensor head housing inlet 110-1 and out of the first sensor head housing 108-1 via the first flow channel 105-1 for detection of smoke particles in the gas.

Similar to the first flow channel 105-1, the second flow channel 105-2 can connect the blower housing 106 to a second sensor head housing 108-2. The second sensor head housing 108-2 can also be configured to receive a sensor head (e.g., not illustrated in FIG. 1A). The second sensor head housing 108-2 can include a second sensor head housing inlet 110-2. The blower can operate to draw gas into another sensor head located in the second sensor head housing 108-2 via the second sensor head housing inlet 110-2 and out of the second sensor head housing 108-2 via the second flow channel 105-2 for detection of smoke particles in the gas.

Figure 1B:
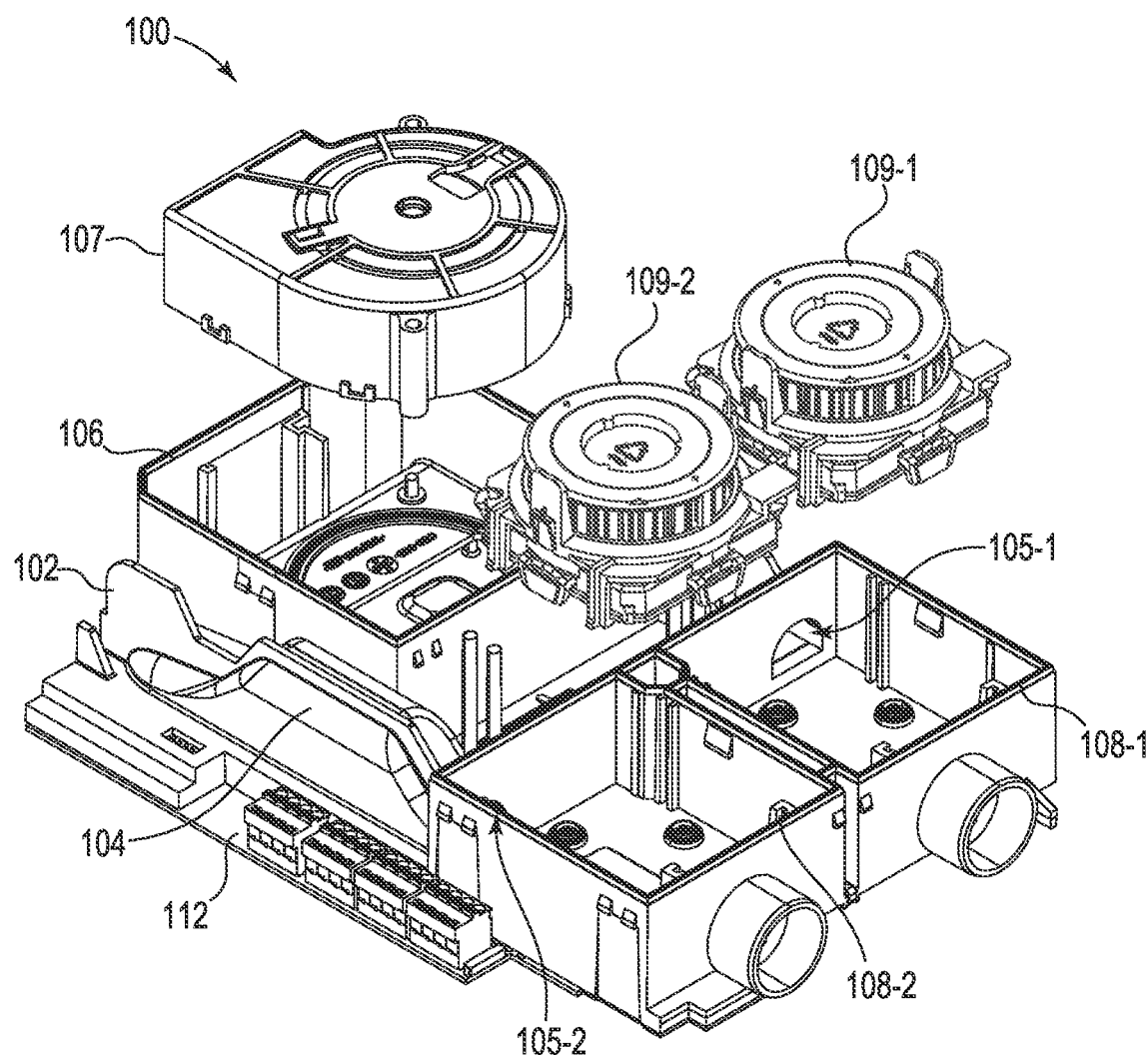
FIG. 1B is an exploded view of an example of a manifold, a blower, and sensor heads of an aspirating smoke detector device, in accordance with one or more embodiments of the present disclosure.

FIG. 1B is an exploded view of an example of the manifold 102, blower 107, and sensor heads 109 of the aspirating smoke detector device 100, in accordance with one or more embodiments of the present disclosure. As previously described in connection with FIG. 1A, the aspirating smoke detector device 100 can include a manifold 102, the manifold including a flow path 104, a blower housing 106, a first sensor head housing 108-1, and a second sensor head housing 108-2. The flow path 104 can include the first flow channel 105-1 and the second flow channel 105-2.

As illustrated in FIG. 1B, the blower housing 106 is configured to receive the blower 107. As used herein, the term "blower" refers to a mechanical device for moving gas in a particular direction. For example, the blower 107 can be utilized to move gas through the aspirating smoke detector device 100. The blower 107 can, in some instances, comprise a ducted housing having a fan that, when spinning, causes gas (e.g., such as air) to flow in a particular direction.

The blower housing 106 is configured to receive the blower 107 when the blower 107 is oriented in a particular configuration. For example, the blower housing 106 can be designed such that the blower 107 can fit into the blower housing 106 in a single orientation. This can prevent the blower 107 from being installed in the blower housing 106 in an incorrect orientation.

The manifold 102 can additionally include the first sensor head housing 108-1. The first sensor head housing 108-1 can be connected to the blower housing 106 via the first flow channel 105-1 and can receive a first sensor head 109-1. As used herein, the term "sensor head" refers to a device to detect events and/or changes in its environment and transmit the detected events and/or changes for processing and/or analysis. For example, the sensor heads 109 can be utilized to detect smoke particles in gas transiting through the aspirating smoke detector device 100. In some examples, the first sensor head 109-1 can be a nephelometer (e.g., an aerosol photometer) to measure the concentration of smoke particles in a gas by utilizing light scattered by smoke particles. However, the first sensor head 109-1 can be any other type of smoke detection sensor that detects smoke utilizing gas transiting through the aspirating smoke detector device 100.

The first sensor head housing 108-1 can be configured to receive a first sensor head 109-1. For instance, the first sensor head housing 108-1 is configured to receive the first sensor head 109-1 when the first sensor head 109-1 is oriented in a particular configuration. For example, the first sensor head housing 108-1 can be designed such that the first sensor head 109-1 can fit into the first sensor head housing 108-1 in a single orientation. This can prevent the first sensor head 109-1 from being installed in the first sensor head housing 108-1 in an incorrect orientation.

Similar to the first sensor head housing 108-1, the second sensor head housing 108-2 can be connected to the blower housing 106 via the second flow channel 105-2 and can receive a second sensor head 109-2. The second sensor head 109-2 can be a nephelometer or any other type of smoke detection sensor that detects smoke utilizing gas transiting through the aspirating smoke detector device 100. Additionally, the second sensor head housing 108-2 can be configured to receive the second sensor head 109-2. For instance, the second sensor head housing 108-2 is configured to receive the second sensor head 109-2 when the second sensor head 109-2 is oriented in a particular configuration. For example, the second sensor head housing 108-2 can be designed such that the second sensor head 109-2 can fit into the second sensor head housing 108-2 in a single orientation. This can prevent the second sensor head 109-2 from being installed in the second sensor head housing 108-2 in an incorrect orientation.

Figure 1C:
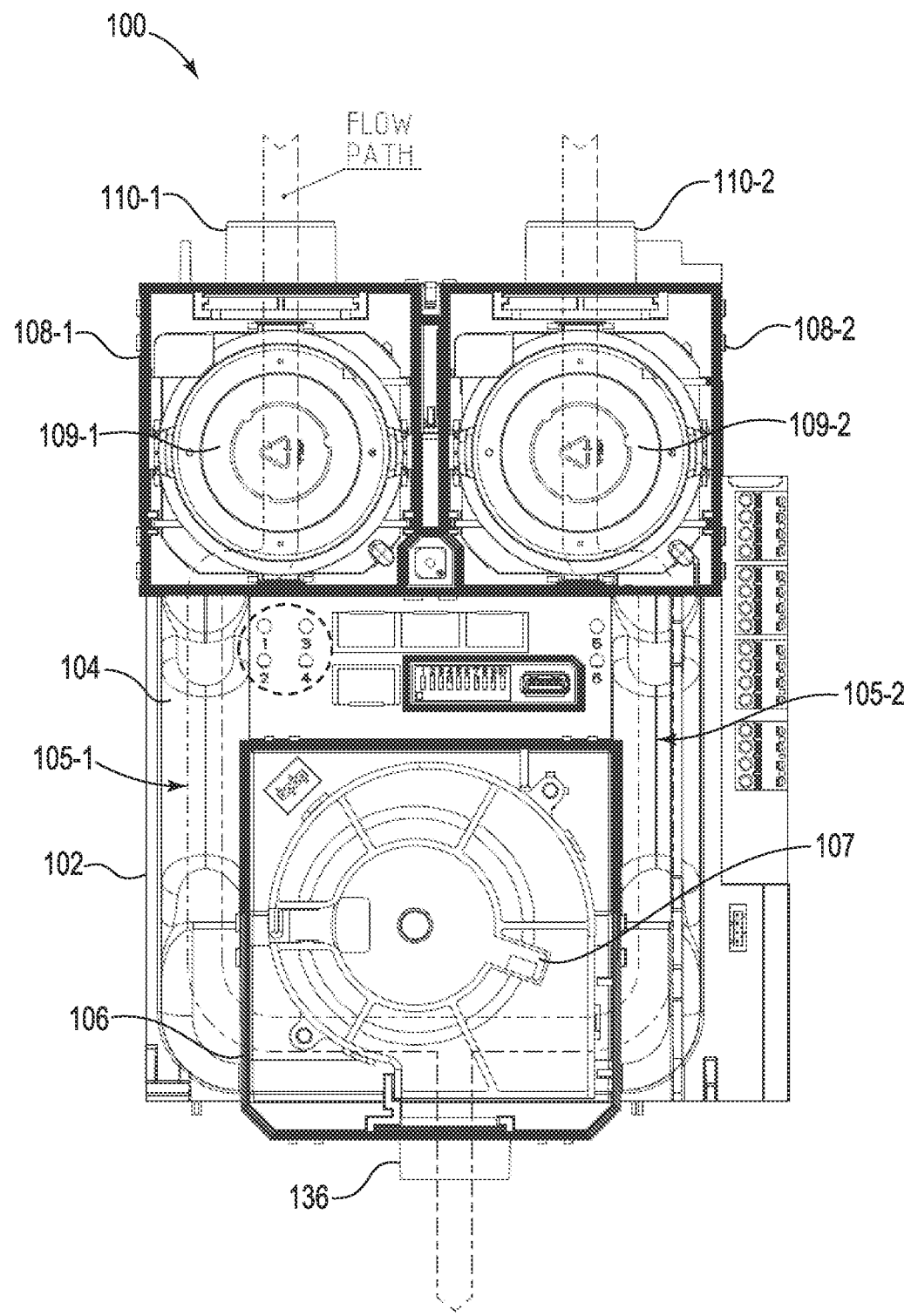
FIG. 1C is a front view of an example of a manifold of an aspirating smoke detector device and its flow channels, in accordance with one or more embodiments of the present disclosure.

FIG. 1C is a front view of an example of the manifold 102 of the aspirating smoke detector device 100 having flow channels 105, in accordance with one or more embodiments of the present disclosure. As previously described herein, the manifold 102 can include a first sensor head housing 108-1, a second sensor head housing 108-2, and a blower housing 106. The first sensor head housing 108-1 can include a first sensor head 109-1 and a first sensor head housing inlet 110-1. The second sensor head housing 108-2 can include a second sensor head 109-2 and a second sensor head housing inlet 110-2. The blower housing 106 can include a blower 107.

When the blower 107 is operating, gas can flow through the aspirating smoke detector device 100 as indicated in FIG. 1C. Gas (e.g., such as air from a space in a facility) can enter the aspirating smoke detector device 100 via the first sensor head housing inlet 110-1 and/or the second sensor head housing inlet 110-2 for smoke particle detection by the first sensor head 109-1 located in the first sensor head housing 108-1 and/or the second sensor head 109-2 located in the second sensor head housing 108-2. Following smoke particle detection by the first sensor head 109-1 and/or the second sensor head 109-2, the gas can travel through the first flow channel 105-1 and/or the second flow channel 105-2 of the manifold 102 and exit the aspirating smoke detector device 100 via the blower housing outlet 136.

Figure 2:
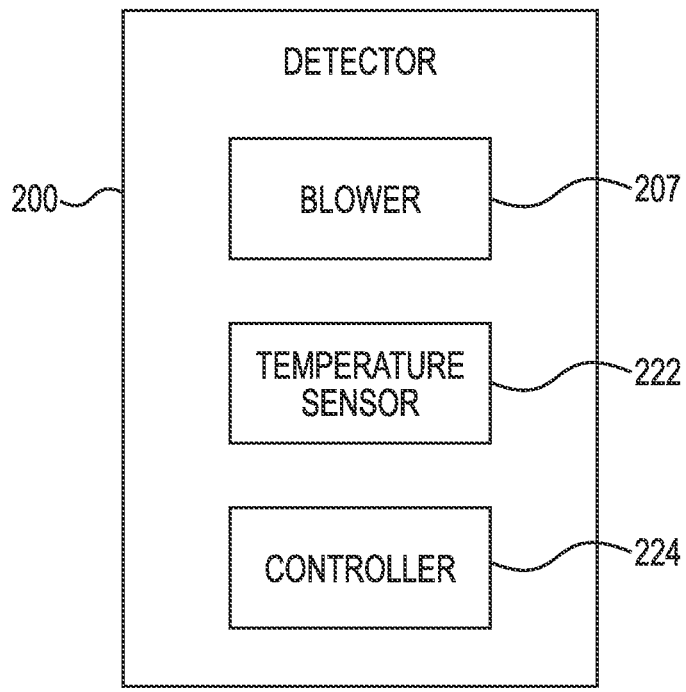
FIG. 2 is a block diagram of an aspirating smoke detector device, in accordance with one or more embodiments of the present disclosure.

FIG. 2 is a block diagram of an aspirating smoke detector device 200, in accordance with one or more embodiments of the present disclosure. Aspirating smoke detector device 200 can be, for instance, aspirating smoke detector device 100 previously described in connection with FIGS. 1A-1C. For example, aspirating smoke detector 200 can include a blower 207, which can be analogous to blower 107 previously described in connection with FIGS. 1A-1C. For instance, blower 207 can cause air to flow through aspirating smoke detector 200, as previously described in connection with FIGS. 1A-1C.

As shown in FIG. 2, aspirating smoke detector device 200 can include a temperature sensor 222. Temperature sensor 222 can measure the temperature of the air flowing through aspirating smoke detector device 200. For example, temperature sensor 222 can be located in the flow channels of aspirating smoke detector device 200 (e.g., in flow channels 105 previously described in connection with FIGS. 1A-1C), and measure the temperature of the air flowing through the flow channels.

Temperature sensor 222 can be, for example, an ultrasonic sensor (e.g., the temperature of the air flowing through the flow channels can be measured using an ultrasonic sensor). However, embodiments of the present disclosure are not limited to a particular type of temperature sensor. Further, although one temperature sensor 222 is shown in FIG. 2 for clarity and so as not to obscure embodiments of the present disclosure, aspirating smoke detector device 200 can include any number of temperature sensors analogous to temperature sensor 222.

As shown in FIG. 2, aspirating smoke detector device 200 can include a controller 224. Controller 224 can be included on, and/or be a part of, a PCB of aspirating smoke detector device 200 (e.g., PCB 112 previously described in connection with FIGS. 1A-1C), as previously described herein. Controller 224 can be, for example, a proportional-integral-derivative (PID) controller, as will be further described herein (e.g., in connection with FIG. 3).

Although not shown in FIG. 2 for clarity and so as not to obscure embodiments of the present disclosure, controller 224 can include a processor and a memory. The memory can be any type of storage medium that can be accessed by processor to perform various examples of the present disclosure. For example, the memory can be a non-transitory computer readable medium having computer readable instructions (e.g., computer program instructions) stored thereon that are executable by the processor to adjust (e.g., compensate) for air flow temperature changes in aspirating smoke detector device 200 in accordance with the present disclosure. That is, the processor can execute the executable instructions stored in the memory to adjust for air flow temperature changes in aspirating smoke detector device 200 in accordance with the present disclosure.

The memory can be volatile or nonvolatile memory. The memory 222 can also be removable (e.g., portable) memory, or non-removable (e.g., internal) memory. For example, the memory can be random access memory (RAM) (e.g., dynamic random access memory (DRAM), resistive random access memory (RRAM), and/or phase change random access memory (PCRAM)), read-only memory (ROM) (e.g., electrically erasable programmable read-only memory (EEPROM) and/or compact-disk read-only memory (CD-ROM)), flash memory, a laser disk, a digital versatile disk (DVD) or other optical disk storage, and/or a magnetic medium such as magnetic cassettes, tapes, or disks, among other types of memory. Further, the memory can be located internal to aspirating smoke detector device 200, or located internal to another computing resource (e.g., enabling computer readable instructions to be downloaded over the Internet or another wired or wireless connection).

Controller 224 can be operated to adjust (e.g., compensate) for air flow temperature changes is aspirating smoke detector device 200, in order to prevent false air flow faults from occurring. For example, controller 224 can monitor the temperature of the air flowing through aspirating smoke detector device 200 (e.g., by receiving the air temperature measurements from temperature sensor 222), and determine when the temperature of the air flowing through the aspirating smoke detector device 200 has changed (e.g., increased or decreased) by a particular amount (e.g., by a particular number of degrees). The particular amount can be, for instance, ten degrees Celsius. However, embodiments of the present disclosure are not so limited.

As an example, controller 224 can determine when the temperature of the air flow has changed from a reference temperature by the particular amount. The reference temperature can be, for instance, the initial temperature of the air flow through aspirating smoke detector device 200 (e.g., the temperature of the air flow during initialization and/or setup of aspirating smoke detector device 200). The reference (e.g., initial) air flow temperature can be measured by temperature sensor 222 during the initialization and/or setup of aspirating smoke detector device 200, and stored by controller 224 (e.g., in the memory of controller 224).

In response to (e.g., upon) determining the temperature of the air flowing through aspirating smoke detector device 200 has changed by the particular amount, controller 224 can adjust the speed of blower 207 to compensate for the air flow temperature change. For instance, controller 224 can increase the speed of blower 207 in response to determining the air flow temperature has increased by the particular amount, and controller 224 can decrease the speed of the blower 207 in response to determining the air flow temperature has decreased by the particular amount. An example illustrating such an increase to the speed of blower 207 in response to an increase of air flow temperature will be further described herein (e.g., in connection with FIG. 5).

As an example, controller 224 can, in response to determining the air flow temperature has changed by the particular amount, determine the speed to adjust blower 207 to, and adjust the speed of blower 207 to the determined speed. Controller 224 can determine the speed to adjust the blower based on a reference air flow (e.g., reference air flow speed), and the difference (e.g., error) between the reference air flow and the air flow (e.g., air flow speed) of the air flowing through the aspirating smoke detector device 200 when it is determined that the temperature of the air has changed by the particular amount (e.g., the difference between the reference air flow and the current air flow). The reference (e.g., initial) air flow can be set during the initialization and/or setup of aspirating smoke detector device 200, and stored by controller 224 (e.g., in the memory of controller 224). Further, if the speed determined by controller 224 is greater than the maximum speed of blower 207, this may be an indication of an error caused by saturation, and accordingly controller 224 may not adjust the speed of the blower to such a determined speed. The determination of the speed to adjust blower 207 to will be further described herein (e.g., in connection with FIG. 3).

Controller 224 can adjust the speed of blower 207 (e.g., to the determined speed) by adjusting the pulse width modulation (PWM) of blower 207. For example, controller 224 can send the PWM signal (e.g., voltage signal) provided to blower 207, and blower 207 can adjust its speed responsive to the adjustment to the PWM signal.

Adjusting the speed of blower 207 in response to the temperature of the air flowing through aspirating smoke detector device 200 changing by the particular amount can prevent a false air flow fault from being indicated by aspirating smoke detector device 200. For example, adjusting the speed of blower 207 to the speed determined by controller 224 can keep the flow of the air (e.g., the air flow speed) through aspirating smoke detector device 200 within a particular air flow range (e.g., within the upper and lower limits of the range), even though the temperature of the air flow has changed by the particular amount. The particular air flow range can comprise a particular range from a reference air flow (e.g., a reference air flow speed), and can correspond to the air flow fault limits of aspirating smoke detector device 200. The reference (e.g., initial) air flow can be set during the initialization and/or setup of aspirating smoke detector device 200, and stored by controller 224 (e.g., in the memory of controller 224). An example illustrating such an air flow range will be further described herein (e.g., in connection with FIG. 4).

During the subsequent operation of aspirating smoke detector device 200, controller 224 can continue to adjust the speed of blower 207 in an analogous manner each time the temperature of the air flowing through aspiration smoke detector device 200 changes by the particular amount. For example, after the speed of blower 207 has been adjusted to the determined speed by controller 224, the temperature of the air flow may once again change by the particular amount. Controller 224 can determine that this additional temperature change has occurred, determine a different (e.g., new) speed to adjust blower 207 to in response to determining this additional temperature change has occurred, and adjust the speed of blower 207 to this different speed, in a manner analogous to that previously described herein. An example illustrating such additional blower speed adjustments will be further described herein (e.g., in connection with FIG. 5). In such a manner, controller 224 can continue to compensate for additional temperature changes that may occur in the air flowing through aspirating smoke detector device 200 throughout its operation, and accordingly may continue to prevent the occurrence of false air flow faults.

Figure 3:
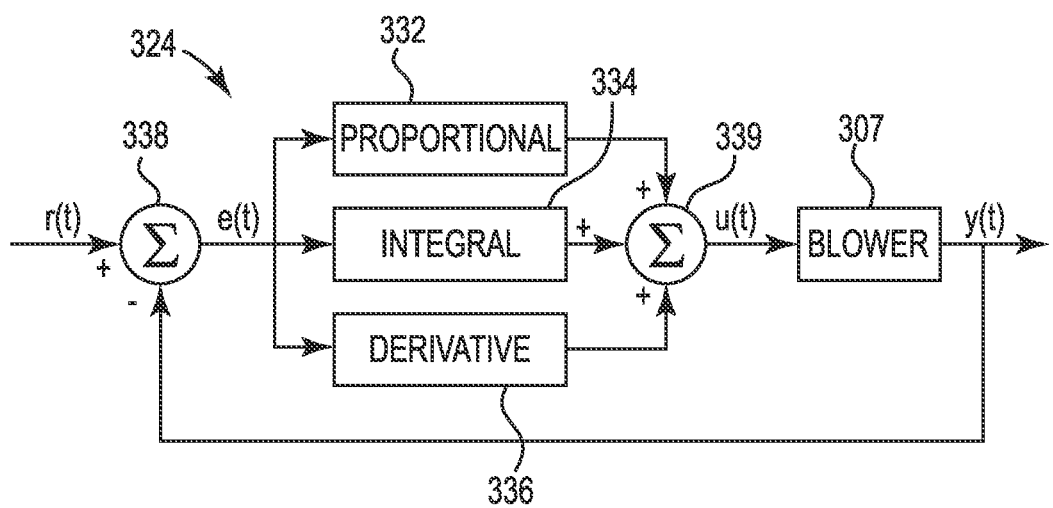
FIG. 3 is a block diagram of a controller of an aspirating smoke detector device, in accordance with one or more embodiments of the present disclosure.

FIG. 3 is a block diagram of a controller 324 of an aspirating smoke detector device, in accordance with one or more embodiments of the present disclosure. Controller 324 can be, for example, controller 224 of aspirating smoke detector device 200 previously described in connection with FIG. 2.

Controller 324 can be a proportional-integral-derivative (PID) controller. For example, as shown in FIG. 3, controller 324 can include a proportional module 332, an integral module 334, and a derivative module 336. As described herein, a "module" can include computer readable instructions that can be executed by a processing resource to perform a particular function. A module can also include hardware, firmware, and/or logic that can perform a particular function.

As shown in FIG. 3, PID controller 324 can comprise a control loop mechanism that uses feedback to determine the speed to adjust blower 307 (e.g., blower 107 and/or 207 previously described in connection with FIGS. 1 and 2, respectively) to in response to the temperature of the air flowing through the aspirating smoke detector device changing by the particular amount. For example, as illustrated at block 338, PID controller 324 can continuously calculate a difference (e.g., error value e(t)) between the reference air flow (r(t)) of the aspirating smoke detector device and the air flow (y(t)) through the aspirating smoke detector device at a given time t.

PID controller 324 can then apply a correction to the error value e(t) using proportional module 332, integral module 334, and a derivative module 336. The correction applied to the error value e(t) using proportional module 332 can be given by:

$$K_p e(t)$$

where $K_p$ is a proportional gain tuning parameter. The correction applied to the error value e(t) using integral module 334 can be given by:

$$K_i \int_0^t e(t)dt$$

where $K_i$ is an integral gain tuning parameter. The correction applied to the error value e(t) using derivative module 336 can be given by:

$$K_d \frac{de(t)}{dt}$$

where $K_d$ is a derivative gain tuning parameter.

As illustrated at block 339, PID controller 324 can then use a weighted sum of the corrected error values provided by proportional module 332, integral module 334, and derivative module 336 to calculate the speed (u(t)) to which to adjust blower 307. That is, the speed u(t) to adjust the blower to can be given by:

$$K_p e(t) + K_i \int_0^t e(t)dt + K_d \frac{de(t)}{dt}$$

Figure 4:
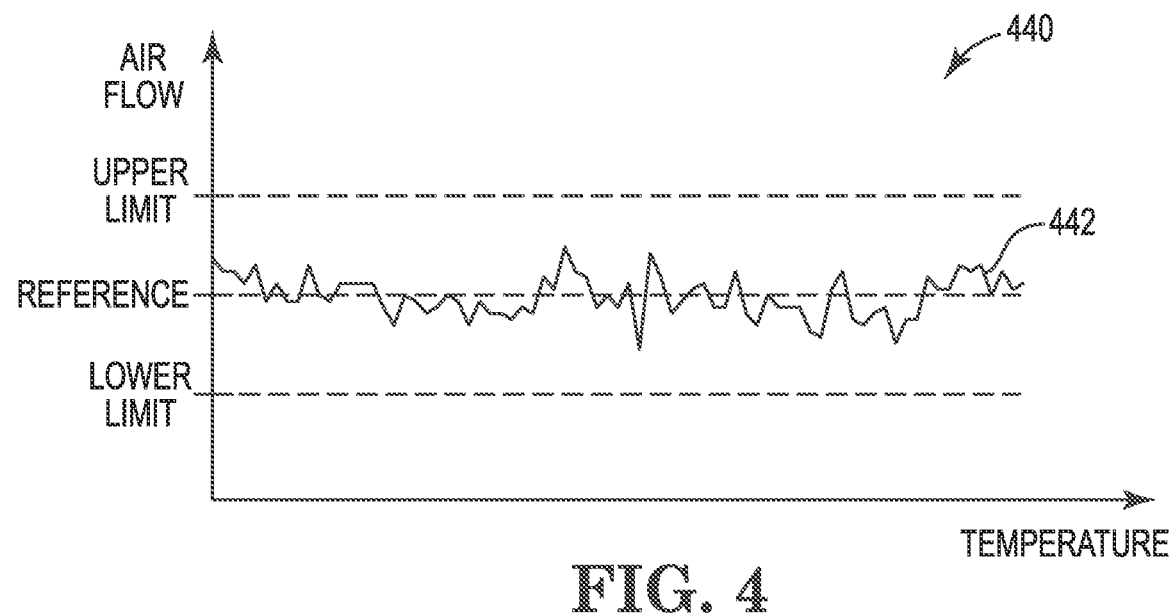
FIG. 4 is a graph illustrating an example air flow range of an aspirating smoke detector device, in accordance with one or more embodiments of the present disclosure.

FIG. 4 is a graph 440 illustrating an example air flow range of an aspirating smoke detector device, in accordance with one or more embodiments of the present disclosure. The aspirating smoke detector device can be, for example, aspirating smoke detector device 100 and/or 200 previously described in connection with FIGS. 1A-1C and 2, respectively.

As shown in FIG. 4, the air flow range comprises the air flow (e.g., air flow speed) values within an upper air flow limit and a lower air flow limit, which are each a particular amount above and below, respectively, a reference air flow value. The air flow range (e.g., the reference air flow value, and the upper and lower air flow limits) can be set during the initialization and/or setup of the aspirating smoke detector device. For instance, the reference air flow value can be set by measuring the air flow through the aspirating smoke detector at a temperature of zero degrees Celsius.

The air flow range can correspond to the air flow fault limits of the aspirating smoke detector device. For example, if, during operation of the aspirating smoke detector device, the air flow through the detector (e.g., through the flow channels of the detector), is detected to exceed the upper air flow limit of the range or fall below the lower air flow limit of the range, this can be an indication of an air flow fault (e.g., an obstacle, leak, etc.), and an air flow fault can be triggered (e.g., indicated by the detector). However, in some instances, the temperature of the air flowing through the detector can change causing the air flow itself to change (e.g., increase or decrease), which if not compensated for can cause a false air flow fault to be detected, as previously described herein.

In the example illustrated in FIG. 4, however, the aspirated smoke detector device has adjusted the speed of its blower to compensate for a change (e.g., increase) of the air flow through the detector caused by a change of the temperature of the air flowing through the detector, in accordance with embodiments previously described herein. Accordingly, the air flow 442 through the aspirated smoke detector device remains within the air flow range (e.g., within the upper and lower limits of the range, near the reference air flow value), even as the temperature of the air increases, as illustrated in FIG. 4, thereby preventing a false air flow fault from occurring.

Figure 5:
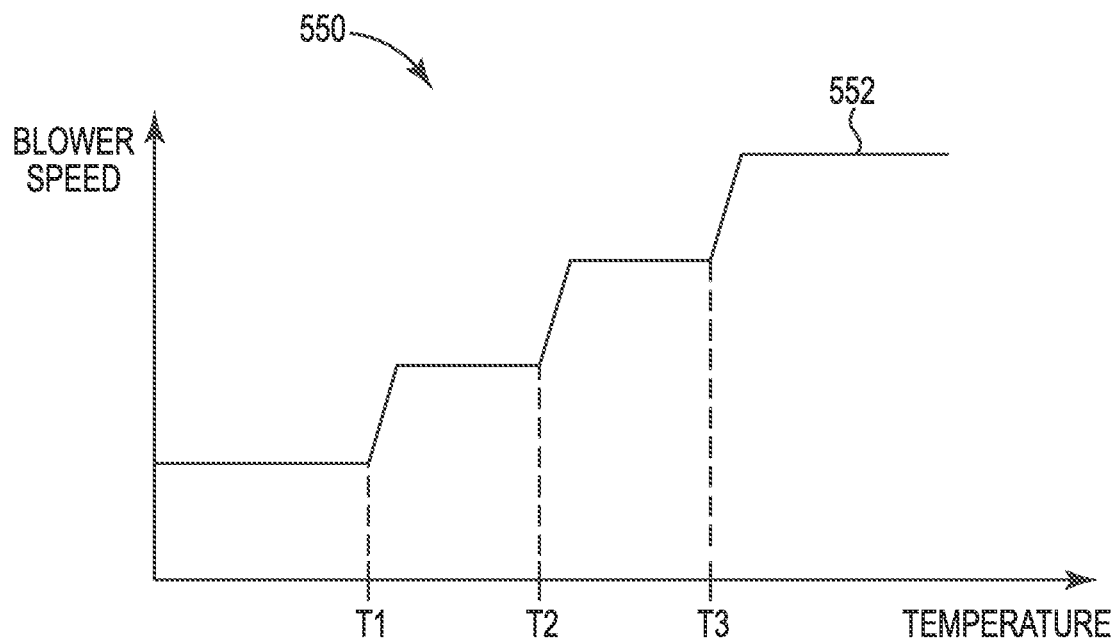
FIG. 5 is a graph illustrating an example of adjustments to the speed of a blower of an aspirating smoke detector device, in accordance with one or more embodiments of the present disclosure.

FIG. 5 is a graph 550 illustrating an example of adjustments (e.g., increases) to the speed of a blower of an aspirating smoke detector device, in accordance with one or more embodiments of the present disclosure. The aspirating smoke detector device can be, for example, aspirating smoke detector device 100 and/or 200 previously described in connection with FIGS. 1A-1C and 2, respectively, and the adjustments to the speed of the blower can be determined and made by controller 224 and/or 324 as previously described in connection with FIGS. 2 and 3, respectively.

In the example illustrated in FIG. 5, the speed (e.g., revolutions per minute) of the blower is increased each time the temperature of the air flowing through the aspirating smoke detector device (e.g., through the flow channels of the detector) increases by a particular amount. For instance, the blower speed 552 is a first speed when the temperature of the air flowing through the detector is at zero degrees Celsius, and remains at the first speed until the air temperature reaches temperature T1. Upon the temperature of the air flowing through the detector reaching T1, the blower speed 552 is increased to a second speed. The blower speed 552 then remains at the second speed until the air temperature reaches temperature T2, at which point the blower speed 552 is increased to a third speed. The blower speed 552 remains at the third speed until the air temperature reaches temperature T3, at which point the blower speed 553 is increased to a fourth speed. Increasing the blower speed 552 each time the temperature of the air flowing through the aspirating smoke detector device increases by the particular amount, as illustrated in FIG. 5, can prevent false air flow faults from occurring, as previously described herein.

The particular amount by which the temperature has increased each time the blower speed 552 is increased can be, for example, ten degrees Celsius. For instance, T1 can be 10 degrees Celsius, T2 can be 20 degrees Celsius, and T3 can be 30 degrees Celsius. However, embodiments of the present disclosure are not limited to this example. Further, although the blower speed 552 is increased by the same amount each time in the example illustrated in FIG. 5, embodiments of the present disclosure are not so limited. For instance, the blower speed may increase by a greater amount upon the air temperature reaching T3 than the amount increased upon the air temperature reaching T1 and T2.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. An aspirating smoke detector, comprising:
   a blower configured to cause air to flow through the aspirating smoke detector; and
   a controller configured to:
   determine a temperature of the air flowing through the aspirating smoke detector has changed by a particular amount; and
   adjust a speed of the blower from a first speed to a second speed in response to compensate the air flowing through the aspirating smoke detector that has changed by the particular amount, wherein the speed of the blower remains at the first speed, and is not adjusted from the first speed to the second speed, until the temperature of the air flowing through the aspirating smoke detector has changed by the particular amount.

2. The aspirating smoke detector of claim 1, wherein the controller is configured to:
   determine the second speed to adjust the speed of the blower to in response to determining the temperature of the air flowing through the aspirating smoke detector has changed by the particular amount.

3. The aspirating smoke detector of claim 1, wherein the controller comprises a proportional-integral-derivative (PID) controller.

4. The aspirating smoke detector of claim 1, wherein the aspirating smoke detector further comprises an ultrasonic sensor configured to measure the temperature of the air flowing through the aspirating smoke detector.

5. The aspirating smoke detector of claim 1, wherein the controller is configured to adjust the speed of the blower by adjusting a pulse width modulation of the blower.

6. The aspirating smoke detector of claim 1, wherein the controller is configured to determine the temperature of the air flowing through the aspirating smoke detector has changed from an initial temperature of the air flowing through the aspirating smoke detector by the particular amount.

7. The aspirating smoke detector of claim 6, wherein the initial temperature is zero degrees Celsius.

8. The aspirating smoke detector of claim 6, wherein the controller is configured to store the initial temperature of the air flowing through the blower.

9. A method of operating an aspirating smoke detector, comprising:
   monitoring, by a controller of the aspirating smoke detector, a temperature of air flowing through the aspirating smoke detector; and
   adjusting, by the controller, a speed of a blower of the aspirating smoke detector from a first speed to a second speed in response to the temperature of the air flowing through the aspirating smoke detector changing by a particular amount, wherein the speed of the blower remains at the first speed, and is not adjusted from the first speed to the second speed, until the temperature of the air flowing through the aspirating smoke detector has changed by the particular amount.

10. The method of claim 9, wherein adjusting the speed of the blower in response to the temperature of the air changing by the particular amount prevents a false air flow fault from being indicated by the aspirating smoke detector.

11. The method of claim 9, wherein the method includes receiving, by the controller, the temperature of the air flowing through the aspirating smoke detector from an ultrasonic sensor of the aspirating smoke detector.

12. The method of claim 9, wherein the method includes adjusting, by the controller, the speed of the blower of the aspirating smoke detector in response to each time the temperature of the air flowing through the aspirating smoke detector changes by the particular amount.

13. The method of claim 9, wherein the particular amount is ten degrees Celsius.

14. A non-transitory computer readable medium having computer readable instructions stored thereon that are executable by a processor to:
   determine a temperature of air flowing through an aspirating smoke detector has changed by a particular amount while a blower of the aspirating smoke detector is operating at a first speed;
   determine a second speed to adjust the blower of the aspirating smoke detector to in response to determining the temperature of the air flowing through the aspirating smoke detector has changed by the particular amount; and
   adjust a speed of the blower to the determined second speed, wherein the speed of the blower remains at the first speed, and is not adjusted from the first speed to the second speed, until the temperature of the air flowing through the aspirating smoke detector has changed by the particular amount.

15. The computer readable medium of claim 14, wherein adjusting the speed of the blower to the determined second speed keeps a flow of the air through the aspirating smoke detector within a particular airflow range.

16. The computer readable medium of claim 15, wherein the particular airflow range comprises a particular range from a reference airflow.

17. The computer readable medium of claim 15, wherein the instructions are executable by the processor to set the particular airflow range during an initialization of the aspirating smoke detector.

18. The computer readable medium of claim 14, wherein the instructions are executable by the processor to:
   determine the air flowing through the aspirating smoke detector has changed by the particular amount while the blower is operating at the second speed;
   determine a third speed to adjust the blower to in response to the air flowing through the aspirating smoke detector having changed by the particular amount after the speed of the blower has been adjusted to the determined second speed; and adjust the speed of the blower to the determined third speed, wherein the speed of the blower remains at the second speed, and is not adjusted from the second speed to the third speed, until the temperature of the air flowing through the aspirating smoke detector has changed by the particular amount.

19. The computer readable medium of claim 14, wherein the instructions are executable by the processor to determine the second speed to adjust the blower to based on:
   a reference airflow; and
   a difference between the reference airflow and an airflow of the air flowing through the aspirating smoke detector when it is determined the temperature of the air has changed by the particular amount.

20. The computer readable medium of claim 14, wherein the instructions are executable by the processor to not adjust the speed of the blower to the determined second speed if the determined second speed is greater than a maximum speed of the blower.

* * * * *